United States Patent [19]

Heine

[11] 4,359,389
[45] Nov. 16, 1982

[54] METHOD FOR THE PURIFICATION OF INTERFERON

[75] Inventor: Jochen W. Heine, North Chicago, Ill.

[73] Assignee: Stichting Rega V.Z.W., Leuven, Belgium

[21] Appl. No.: 198,223

[22] Filed: Oct. 17, 1980

[30] Foreign Application Priority Data

Oct. 23, 1979 [NL] Netherlands .................. 7907791

[51] Int. Cl.³ .............................................. B01D 15/08
[52] U.S. Cl. ................................... 210/644; 210/656; 424/85; 435/811; 260/112 R
[58] Field of Search ............... 210/635, 656, 659, 644; 435/811; 424/85; 260/112 A

[56] References Cited

U.S. PATENT DOCUMENTS

| 3,560,611 | 2/1971 | Chany | 435/811 |
| 4,070,284 | 1/1978 | Fujita | 210/659 |
| 4,168,261 | 9/1979 | Edy | 424/85 |
| 4,266,024 | 5/1981 | Swetly | 435/811 |

OTHER PUBLICATIONS

Cantell et al., In Vitro, 3, 35–38 (1974).
A. Billiau et al., J. Gen. Virol, 19, 1–8 (1973).
Strander et al., J. Clin. Microbiol. 1, 116–117 (1975).
A. Billiau et al., Antimicrobial Agents & Chemotherapy, 16, 49–55, 56–63 (1979) compare Chemical Abstracts, 91, 138651y.
V. G. Edy et al., J. Biol. Chem., 252, 5934–5935 (1977), compare Chem. Abstracts 87, 150022u.
Science, 130, 432–437 (1959).
W. Haller, Nature, 206, 693–696 (1965).
H. G. Bock et al., Science, 191, 380–383 (1976).
R. Dulbecco et al., J. Exp. Med., 99, 167–182 (1954).
J. Porath et al., Nature, 258, 598–599 (1975).
W. J. Jankowski et al., Biochemistry, 15, 5182–5187 (1976).

*Primary Examiner*—John Adee
*Attorney, Agent, or Firm*—Birch, Stewart, Kolasch & Birch

[57] ABSTRACT

Human fibroblast interferon may be purified to a high degree by using a simple two-step purification method comprising (a) subjecting an aqueous interferon solution to chromatography on porous glass beads, and (b) subjecting the resulting aqueous interferon solution to chromatography on immobilized zinc chelate. Overall recoveries of about 45–76% of the initial interferon activity may be achieved and the end product will be free of any skin reactive agents.

14 Claims, No Drawings

METHOD FOR THE PURIFICATION OF INTERFERON

BACKGROUND AND SUMMARY OF THE INVENTION

Interferon is a glycoprotein produced by living cells in defense against virus infection. Its chemical structure may vary slightly depending upon the cell type that is used for its production. This interferon has various biochemical activities, such as antiviral, antiprotozoal, cell growth inhibitory and immunosuppressive activities and may, therefore, be applied successfully in medicine. For a general review of the present knowledge of interferon, reference may be made to the book "Interferons and their actions" by W. E. Stewart II, CRC Press, Inc., Cleveland, Ohio.

For medical application in human patients, interferon should be prepared from human cells and the following methods for this purpose are now in use:

1. Production by infection of freshly collected leukocytes from human blood donors with Sendai-virus. This results in the so-called leukocyte interferon as described by Cantell et al, In vitro, 3, 35–38, (1974).

2. Production on cultivated diploid human fibroblast cells with the aid of a so-called "Poly-I:C-superinduction schedule". The resulting fibroblast interferon differs from leukocyte interferon by several biological and physiochemical criteria (see A. Billiau et al, J. Gen. Virol., 19, 1–8, (1973)).

3. Production in lymphoblastoid cell lines using a viral interferon inducer. The resulting lymphoblast interferon has a strong resemblance to leukocyte interferon (see Strander et al, J. Clin. Microbiol., 1, 116–117, (1975)).

The present invention relates to human fibroblast interferon, that is interferon produced by the second of the above-mentioned methods, and more specifically, it relates to a method for the purification of such interferon.

Purification of interferon is necessary both for studies on the chemical character of interferon and for clinical application thereof, since a crude interferon solution may contain contaminating proteins that have a negative effect on the results of such studies and application. For both purposes, rather large amounts of purified interferon are needed. Although many techniques for partial purification and a few techniques for complete purification of interferon have been described, all of them suffer from deficiencies. These deficiencies are in general, either the necessity of using complex adsorbents or reagents, or the use of a multiple step procedure which is not applicable to large scale production, or the fact that only a small fraction of the total initial interferon activity is recovered in purified form.

Therefore, a need exists for a purification method of interferon, and especially a purification method of human fibroblast interferon, which leads to a high recovery of activity in purified form, which does not require complex reagents or a complexity of steps, and which is capable of being used on a rather large scale.

As a result of extensive research, it has now been found that a high recovery of interferon activity in the form of completely purified interferon may be obtained by treating human fibroblast interferon with a simple two-step purification method which is a combination of two earlier known methods. This two-step purification method comprises (a) subjecting an aqueous interferon solution to chromatography on porous glass beads, and (b) subjecting the resulting aqueous interferon solution to chromatography on immobilized zinc chelate.

If, in the first step, an interferon solution containing contaminating proteins is contacted with porous glass beads at neutral or slightly alkaline pH, the interferon will be selectively adsorbed onto these glass beads and the bulk of contaminating proteins will remain in solution and may be washed away. The adsorbed interferon may thereafter be eluted from the glass beads at an acidic pH.

If thereupon, in the second step, the eluted interferon solution is contacted with an immobilized zinc chelate gel at neutral or slightly alkaline pH, the interferon will be selectively adsorbed onto this zinc chelate and contaminating proteins that might still be present will remain in solution and may be washed away. The adsorbed interferon may thereafter be eluted from the zinc chelate at acidic pH and will result in an end product of extremely high purity.

By using this two-step purification method, a high degree of purification may be reached since the end product is of such high purity that it may be considered to be substantially completely pure. Further, a high recovery of initial interferon activity may be achieved. This recovery will be about 50–70% in the first step, and 90–95% in the second step, thus resulting in an overall recovery of about 45–67%.

A special advantage is that the end product of the invented purification method will be free of any skin reactive agent. The products of earlier purification methods always incited skin reactions upon clinical application to patients but it has appeared that the product of the present invention will not incite such reactions and this is quite important for clinical use.

A further advantage is that the reagents are easily available and may be used many times in succession since both the glass beads and the immobilized zinc chelate may be reclaimed or regenerated after use. Further, the invented method uses only two steps and all these facts result in a simple method that can be used on a rather large scale.

Thus, the invention provides a method for the purification of interferon, which comprises (a) subjecting an aqueous solution of human fibroblast interferon to chromatography on porous glass beads, and (b) subjecting the resulting interferon solution to chromatography on immobilized zinc chelate.

It should be noted here that both steps of the invented method are known individually and have been used earlier for purification of human fibroblast interferon. Compare A. Billiau et al, Antimicrobial Agents and Chemotherapy, 16, 49–55 (1979) for the first step, and V. G. Edy et al, J. Biol. Chem. 252, 5934–5935 (1977) for the second step. At the time of these publications, however, the said steps were used quite independently and there was nothing to suggest that a substantially complete purification would be brought about by combining these steps in a simple two-step method.

Moreover, several other methods are known for purification of interferon and it would be impossible to predict that a combination of the aforesaid two steps without necessity of adding further steps, would lead to the desired result. Further, the absence of any skin reactivity in the end products of the invented method can be termed surprising and unexpected because until now, all purified fibroblast interferon showed such skin reactivity upon clinical application to patients (compare A. Billiau et al, Antimicrobial Agents and Chemotherapy, 16, 56–63 (1979)).

Furthermore, it should be noted that the combination of both steps in a two-step method has led to a slight modification of the first step; as far as the eluate of the glass beads is concerned. In the above-mentioned first Billiau paper, this eluate was dialyzed against polyethyleneglycol in a sodium acetate buffer in order to prepare it for lyophilization and clinical use. In the present invention, however, such eluate will be dialyzed against a phosphate buffer in order to prepare it for chromatography in the next purification step, as will be described later on in this specification.

DETAILED DESCRIPTION OF THE INVENTION

The method of the invention will now be described in more detail.

The starting solution for the invented purification method may be any aqueous solution of human fibroblast interferon which contains contaminating proteins and which will need purification. Such solution may result from a conventional production method of the interferon and from any stage thereof. It should be noted that the method is applicable to human fibroblast interferon only and that other interferon types will need a different purification method.

Although the starting solution may comprise any aqueous medium for keeping the interferon in solution, good results have been obtained with a solution of interferon in Eagles's minimal essential medium (compare Science, 130, 432 (1959)). A stabilizer may be added to this medium, if desired, and the preferred stabilizer in this respect is a human plasma protein fraction such as supplied by blood banks.

The initial protein content and interferon activity of the starting solution are not bound to critical limits. However, the solution may be diluted or concentrated first, if the protein content is deemed to be so high as to render a risk of precipitation or to be so low as to render the method uneconomical. It should be noted here that the amount of contaminating proteins may exceed that of the interferon and that it may well be over 85% of the total amount of dissolved substances.

The first step of the invented method comprises chromatography on porous glass beads. Such porous glass beads are available on the market under several Trade marks and are frequently indicated as having a "controlled pore size", i.e. a rather uniform pore size concentrated around a specific average value. Such average value may be e.g. 350 or 900 A although in general any value from 170–1700 A or more may be used (compare W. Haller, Nature, 206, 693–696 (1965) and H. G. Bock et al, Science, 191, 380–383 (1976)). The bead diameter may be less uniform and may range in general between about 50 μm and about 500 μm. These beads may be packed in columns but it will be more easy to use them in free form for batch-type operation.

In the first step of the method, the starting solution is contacted with the porous glass beads for selective adsorption of interferon onto the beads. Such contact may be most economically effected by shaking the starting solution with an amount of glass beads in a container, but passing the starting solution over a column packed with glass beads is also possible. The contact leads to an adsorption of interferon from the solution onto the glass beads while the bulk of contaminating proteins which are present in the starting solution will not be bound by the beads and will remain in solution.

The pH during contact will be the pH of the starting solutin. This pH will normally be about 7.4 if Eagle's minimal essential medium has been used although in general the system will work well for starting pH's between 7.0 and 8.2. Above pH 8.2, part of the interferon is inactivated and below pH 7.0 much of the applied interferon is not adsorbed onto the glass beads.

The duration of the contact is not bound to critical limits although it should of course be sufficient to have nearly all interferon absorbed onto the beads. This duration may normally vary between 0.5 and 26 hours.

After contact, the remaining solution may be removed, e.g. by decantation or by discharging. Then, the glass beads may be washed with a conventional washing fluid such as a phosphate-buffered saline solution of substantially neutral pH to remove any unbound contaminating proteins. The molar strength of this fluid should be rather low in order to prevent elution of adsorbed interferon. Good washing results have been obtained with a phosphate-buffered saline solution containing Ca and Mg salts (compare R. Dulbecco et al, J. Exp. Med., 99, 167–182 (1954)) but other fluids may be used with the same effect. Further washings may be effected with a special buffer solution of lower pH, such as a 0.01 M glycine-HCl buffer of pH 3.5 for removing any contaminating proteins that inadvertently have been bound to the column. The pH of this washing fluid should not be lower than about 3.0 and its ionic strength should not be higher than about 0.05 M since lower pH values and higher ionic strengths would provoke the elution of large amounts of interferon.

After the washing step, the adsorbed interferon may be eluted from the glass beads with the aid of an acidic aqueous buffer solution. This solution should in general have a pH between 1.5 and 2.7 and preferably a pH of 2.0. No good elution will be obtained at pH values above 2.7 and instability of the eluted interferon will be caused at pH values below 1.5. The ionic strength (molarity) of the eluting solution is somewhat less critical and may vary in practice between 0.05 M and 0.5 M. Values below 0.05 M will tend to give insufficient buffering, thus resulting in a loss of pH control, and higher values than 0.5 M will tend to result in crystallization of constituents.

Any suitable water-soluble buffering agent, or combination of agents, may be used for elution, provided that the aforesaid requirements of pH and ionic strength are satisfied. Thus, the eluting solution may contain a combination of an aminoacid and an inorganic acid, or a combination of an inorganic salt and an inorganic acid, or any other combination or single substance. Good results have been obtained with a 0.1 M KCl-HCl buffer solution of pH 2.0 and still better results with a 0.3 M glycine-HCl buffer solution of pH 2.0. Further, the elution solution may contain a suitable stabilizer, e.g. in the form of a human plasma protein fraction, as mentioned above.

With the aid of such an acidic eluant, substantially all of the adsorbed interferon may be eluted from the glass beads.

After elution, the glass beads may be washed and reclaimed, e.g. by rinsing them with strong acids for several days or heating them on a steam bath with 10% nitric acid, in both cases followed by repeated washing with water to neutrality. Thereafter, they may be used again for chromatography of interferon in the above-described way.

The result of the eluting treatment is an aqueous interferon solution which comprises the major part of the interferon activity of the starting solution and which further comprises only a small proportion of contaminating proteins. In practice, the recovery of interferon activity in this first step of the invented method will range from 50 to 70% and the specific activity of the product per milligrams of protein will be substantially increased in view of the starting material.

The eluate as obtained in the first step has an acidic pH and comprises glycine or another substance which makes it less suitable for immediate use in the second step. Therefore, it should be neutralized and freed of glycine before further processing. This can be achieved by dialyzing the eluate against a phosphate-buffered saline solution of substantially neutral pH. Good results have been obtained here by using a buffer solution containing 0.02 M sodium phosphates (disodium and monosodium) and 1 M sodium chloride of pH 7.4 but other buffer solutions may be equally suitable. The high content of sodium chloride in this buffer solution will be transmitted to the interferon solution and will have a favorable effect during the next step.

The second step of the invented method comprises chromatography on immobilized zinc chelate.

The starting solution for this second step is an aqueous solution of human fibroblast interferon such as resulting from the above-mentioned first step after neutralization and removal of glycine. This solution may be diluted or concentrated if desired, but normally such treatments will not be necessary.

Any type of zinc chelate immobilized on a suitable carrier may be used for the second step of the invented method but the preferred material is a zinc chelate of iminodiacetate immobilized on Sepharose (compare J. Porath et al, Nature, 258, 598–599 (1975) and V. G. Edy et al, J. Biol. Chem. 252, 5934–5935 (1977) which are here incorporated by way of reference). Such adsorbant may be produced by first coupling the disodium salt of iminodiacetic acid to epoxy-activated Sepharose (i.e. agarose having side chains with terminal epoxy groups and then introducing zinc ions to be chelated by the iminodiacetate groups. If the coupled material is already packed in a column, the zinc can be introduced easily by passing a zinc chloride solution through the column and the product is immediately ready for use. In this product, the zinc ions are bound by strong bonds and are capable of reversibly binding interferon molecules, the latter process being pH-dependent.

More specifically, the chelated and immobilized zinc ions are capable of binding human fibroblast interferon quite selectively at neutral or slightly alkaline pH and at low ionic strength of mineral additives. Upon reduction of the pH and increase of ionic strength, however, the interferon is eluted. A good elution can be obtained by using a pH gradient at constantly high ionic strength (compare the aforesaid Edy paper).

In the second step of the invented method, the starting solution is contacted with the immobilized zinc chelate for selective adsorption of interferon thereto. Such contact may be effected by passing the starting solution over a column packed with the adsorbant or by shaking it with an amount of adsorbant in a container. The use of a column is preferred here since the adsorbant may easily be prepared in this form as shown above. The contact leads to an adsorption of interferon from solution onto the zinc chelate while contaminating proteins as far as still present will not be bound and will remain in solution.

The pH during contact will normally be 7.4 if the starting solution has been dialyzed against the aforesaid phosphate-buffered saline solution, although in general the system will work at starting pH's from 7.0 to 8.2. Above pH 8.2, some activity is lost and below pH 7.0 much of the interferon is not adsorbed and passes straight through the column.

The duration of contact is not bound to critical limits although it should of course be sufficient to have substantially all interferon adsorbed. This duration may vary between 0.5 and 26 hours.

After contact, the remaining solution is removed and the column may be washed with a conventional washing agent such as a phosphate-buffered solution of pH 7.4 to remove residual unadsorbed proteins from the column. Further washings may be effected with a buffer solution of lower pH such as a 0.1 M sodium acetate/acetic acid solution of pH 5.9 to remove any proteins that have inadvertently been bound to the column. The pH of this buffer solution should not be lower than about 5.9 to prevent elution of interferon. All these washing fluids may contain 1 M sodium chloride, just as the above-mentioned dialyzing fluid in order to prevent non-specific binding of proteins to the adsorbant.

After washing, the interferon may be eluted from the zinc chelate adsorbant with the aid of an acidic aqueous solution. This solution may in general have a pH between 4.0 and 6.0 and for best results, a pH gradient from 6.0 down to 4.0 may be used. Good elution will not be obtained at values above pH 6.0 and instability of the eluted interferon will occur at values below pH 4.0.

The ion strength (molarity) of the eluant is not very critical and may vary in practice between 0.05 M and 0.5 M. Lower values will tend to give insufficient buffering, thus resulting in a loss of pH-control, and higher values will tend to raise difficulties by crystallization of constituents. Good results have been obtained with a 0.1 M sodium acetate solution adjusted with glacial acetic acid to pH 4.2, although other solutions like those mentioned in the Edy paper are not excluded. If this eluant of pH 4.2 is used immediately after the washing fluid of pH 5.9, a pH gradient will be automatically achieved. As an alternative, 0.1 M sodium acetate solutions of gradually decreasing pH could be used in succession. All these eluting solutions should contain 1 M sodium chloride in order to maintain the NaCl equilibrium in the column.

With the aid of such an eluant, substantially all of the adsorbed interferon may be eluted from the zinc chelate adsorbant.

After elution, the adsorbant may be washed and regenerated, e.g. by rinsing the column with a buffered solution of ethylenediamine tetracetate (EDTA), washing out the EDTA with a phosphate-buffered saline solution of pH 7.4, treating the column with an acidic zinc chloride solution until the chelate is saturated again with zinc, and washing out the excess of zinc chloride with a sodium acetate buffer solution and equilibrating the column to substantially neutral pH values.

The result of the elution treatment is an aqueous interferon solution which still comprises all or the majority of the interferon activity of the starting solution and wherein the content of contaminating proteins has been reduced to a very small value. The recovery of interferon activity in the second step may amount to 90 to 95%, thus making the overall recovery of the whole two-step method about 45 to 67%.

The specific activity of the product may amount to $10^9$ units/mg of protein which is higher than any other value obtained until now. The purity of the final interferon solution may be established by several methods. One of these methods is a normal protein assay, e.g. with fluorescamine. Another method comprises labelling the purified interferon with a radioactive tracer such as $^{125}I$ and subjecting the interferon to acrylamide gel electrophoresis followed by X-ray autoradiography. This indicates whether the purified interferon is a single or multiple product. Further, it can be tested whether the final product incites a skin reaction upon application to the human body.

All these methods indicate a very high purity when applied to the end products of the invented purification method. Thus, it is shown e.g. in the Examples of this specification that remaining impurities could not be measured by protein assays, and that the end products appeared to be a homogeneous product by means of electrophoresis. Further, the products did not produce any fever or skin reaction upon application to humans.

In conclusion, the invented two-step purification method leads to a high recovery of initial interferon activity in a very pure form. The product is suitable for clinical therapy owing to the absence of skin reactivity therein. Large scale production has become possible now since the reagents are readily available and easy to regenerate. This means that large amounts of human fibroblast interferon may be supplied in the future, as required for chemical characterization and clinical use.

The invented method will be further illustrated by the following examples which should not limit the scope of the invention.

EXAMPLE I

The starting material was an aqueous interferon solution derived from human embryo fibroblast type cells stimulated with polyinosinic-polycytidylic acid. The interferon was in Eagle's minimal essential medium of pH 7.4, containing 1% by volume of human plasma protein fraction, supplied by the Belgian Red Cross. The interferon activity and protein content of this solution in a small scale experiment are stated in Table A.

This starting solution was mixed with porous glass beads (Electro-Nucleonics Inc) having a pore size of about 350 Å and a bead size of 75 to 120 μm, at a ratio of about 30 ml solution to about 1 ml of glass beads. The mixture was gently agitated for 2 hours in order to keep the beads in suspension and to cause a selective adsorption of interferon from solution onto the beads. Thereupon, the beads were allowed to settle and the supernatant was removed by decantation. The beads were washed twice with a phosphate-buffered saline solution containing 8 g NaCl, 1.15 g $Na_2HPO_4$, 0.2 g $KH_2PO_4$, 0.2 g KCl, 0.12 g $MgSO_4$ and 0.10 g $CaCl_2$ per liter (compare Dulbecco et al, J. Exp. Med., 99, 167–182 (1954)) at a ratio of 20 ml solution per ml of beads. Then, they were washed one time with a 0.01 M glycine-HCl buffer solution of pH 3.5, at the same ratio. The beads were eluted by 2×5 minutes stirring with a 0.3 M glycine-HCl buffer solution of pH 2.0 and 2×30 minutes stirring with the same buffer solution, each time at a ratio of 2 ml buffer solution per ml of beads. This buffer solution contained 0.09 mg/ml of human plasma protein fraction as a stabilizer. The protein content and interferon activity of the combined eluates are shown in Table A and it appears that the recovery of interferon activity in this experiment was 68%.

After elution, the glass beads were regenerated by rinsing with strong acids for several days and subsequent washing with distilled water to neutrality. Before reuse, they were sterilized by autoclaving.

A portion of the combined eluates was dialyzed against 4×500 ml of a phosphate-buffered saline solution containing 0.02 M sodium phosphate and 1.0 M sodium chloride and having a pH of 7.4. This buffer solution was changed every 6–8 hours. As a result, the pH became about 7.4 and the glycine concentration was decreased from 0.3 M to about 0.0001 M, while a sodium chloride content of 1 M was introduced.

The resulting interferon solution was passed at a flow rate of 20 ml/h through an immobilized zinc chelate column of 0.9×8 cm. The immobilized zinc chelate had been prepared by coupling iminodiacetate to epoxy-activated Sepharose 6 B, and adding a zinc chloride solution, as disclosed by Edy et al, in J. Biol. Chem. 252, 5934–5935 (1977).

Following application of the interferon, the column was washed with one bed (10 ml) volume phosphate-buffered saline solution (the same as used for dialysis) to remove unadsorbed proteins. Then, it was washed with 3 bed volumes of a 0.1 M sodium acetate buffer of pH 5.9 containing 1 M sodium chloride for removing any adsorbed undesired proteins.

Then, the column was eluted with 2 bed volumes of 0.1 M sodium acetate buffer solution containing 1 M sodium chloride and showing a pH gradient of 6 to 4. The fractions within a pH range of 5.2 to 4.5 were collected as they contained the bulk of interferon activity.

The protein content and interferon activity of the resulting eluate are shown in Table A. It appears that the recovery of interferon activity in this second step was 94%, thus resulting in an overall recovery of 64%.

The eluate showed a specific interferon activity of about $1.1 \times 10^9$ units/mg which means that the product was of high purity.

The zinc chelate column was regenerated by washing it with 5 bed volumes of 0.05 M EDTA in a phosphate-buffered saline solution of pH 7.4. The remaining EDTA was removed by washing with 5 bed volumes of phosphate-buffered saline solution (pH 7.4). Then, zinc was reintroduced by washing with 0.1 M sodium acetate (pH 4.0) containing 1 M NaCl and 1 mM $ZnCl_2$ until saturation. The saturation point was tested by mixing a drop of the eluate from the column with a small quantity of sodium carbonate solution and observing the formation of a precipitate. Thereafter, the excess of zinc was removed by washing with sodium acetate buffer (pH 4.0) and the column was equilibrated to pH 7.4 for application of a new sample by washing with 5 bed volumes of phosphate-buffered saline solution.

The purity of the end product was tested by protein assay, acrylamide gel electrophoresis, and application to human skin. In the protein assay (fluorescamine method), the amount of protein was nearly unmeasurable (the limit value in this method is about 2 μg per milliliter). Electrophoresis in acrylamide gel after labeling with a radioactive tracer and followed by X-ray autoradiography revealed the existence of only one radioactive band which had a molecular weight of about 22,000. No skin reactivity at all was shown upon application to humans. This leads to the conclusion that the product of this Example was of high purity and could be considered as being completely pure.

TABLE A

| Material | Volume ml | Total protein mg | Total activity units | Spec. activity units/mg |
|---|---|---|---|---|
| Starting solution | 125 | 67.92 | $4 \times 10^6$ | $5 \times 10^4$ |
| Glass beads: | | | | |
| unadsorbed + washings | 300 | 60.81 | 0 | 0 |
| Eluates | 34 | 2.04 | $2.7 \times 10^6$ | $1.5 \times 10^6$ |
| Dialyzed solution | 34 | 2.04 | $2.7 \times 10^6$ | $1.5 \times 10^6$ |
| Zinc chelate: | | | | |
| unadsorbed + 1st washings | 44 | 2.03 | 0 | 0 |
| 2nd washings | 30 | 0 | 0 | 0 |
| Eluates | 3 | ~0.002 | $2.55 \times 10^6$ | $\sim 1.1 \times 10^9$ |

EXAMPLE II

The same starting material as in Example I was used for two large scale experiments. The procedure was similar to that of Example I with the exception that the eluates from the glass beads were dialyzed against $4 \times 4$ liters of phosphate-buffered saline solution, and that a zinc chelate column of $1.5 \times 16$ cm was used. This zinc chelate column (bed volume 30 ml) was washed first with one bed volume of phosphate-buffered saline and then with 5 bed volumes of sodium acetate buffer. Elution was effected with 2 bed volumes of 0.1 M sodium acetate buffer solution of pH 4.2 containing 1 M sodium chloride, which resulted in pH gradient in the eluate. The fractions within the pH range of 5.2 to 4.5 were collected and contained the bulk of interferon activity.

The protein contents and interferon activities of the starting solution and its products are shown in Table B. It appears from this Table that the recovery of interferon activity in the first step was 57.5% and 58% respectively, and in the second step 91.4% and 91.6% respectively, thus resulting in an overall recovery of 52.6% and 53.2% respectively.

The eluates showed a specific interferon activity of about $1.7 \times 10^9$ and $2 \times 10^9$ units/mg which means that the product was of high purity. Further, the purity of the end products was tested in the same way as in Example I and gave similar results. This means that the method of the invention is suitable indeed for large scale operation.

TABLE B

| Material | Volume ml | Total protein mg | Total activity units | Spec. activity units/mg |
|---|---|---|---|---|
| Starting solution | 3200 | 1075.2 | $64 \times 10^7$ | $5.9 \times 10^4$ |
| | 3200 | 1462.9 | $1.5 \times 10^8$ | $10.3 \times 10^4$ |
| Glass beads: | | | | |
| unadsorbed + washings | 4700 | — | — | — |
| | 4700 | — | — | — |
| Eluates | 280 | 124.6 | $3.68 \times 10^7$ | $2.96 \times 10^5$ |
| | 280 | 169.54 | $8.7 \times 10^7$ | $5.13 \times 10^5$ |
| Dialyzed solution | 100 | 44.6 | $1.32 \times 10^7$ | $2.96 \times 10^5$ |
| | 100 | 60.55 | $3.11 \times 10^7$ | $5.14 \times 10^5$ |
| Zinc chelate: | | | | |
| unadsorbed + 1st washings | 130 | 42.51 | 0 | 0 |
| | 130 | 60.01 | 0 | 0 |
| 2nd washings | 150 | 1.60 | $0.76 \times 10^6$ | $0.47 \times 10^6$ |
| 2nd washings | 150 | 1.60 | $0.76 \times 10^6$ | $0.47 \times 10^6$ |
| | 150 | 0.48 | — | — |
| Eluates | 10 | ~0.007 | $12.02 \times 10^6$ | $\sim 1.7 \times 10^9$ |
| | 10 | 0.014 | $2.85 \times 10^7$ | $2 \times 10^9$ |

What we claim is:

1. A method for the purification of interferon, by chromatography comprising the steps of:
   (a) contacting an aqueous solution of human fibroblast interferon with porous glass beads at neutral or slightly alkaline pH for selective adsorption of interferon from solution onto the beads;
   (b) contacting the beads with an elution agent at acidic pH for elution of adsorbed interferon from said beads;
   (c) collecting a first interferon-containing eluate;
   (d) contacting said eluate with immobilized zinc chelate at neutral or slightly alkaline pH for selective adsorption of interferon from said eluate onto said zinc chelate;
   (e) contacting said zinc chelate with an elution agent at acidic pH for elution of interferon from said chelate; and
   (f) recovering a second eluate containing purified interferon.

2. The method of claim 1, characterized in that the glass beads after adsorption and before elution are washed with a phosphate-buffered saline solution of about neutral pH followed by washing with a buffer solution of lower pH up to pH 3.0.

3. The method of claim 1, characterized in that the elution agent of step (b) has a pH between 1.5 and 2.7 and an ionic strength between 0.05 M and 0.5 M.

4. The method of claim 3, characterized in that elution from the glass beads is effected with a 0.3 M glycine-HCl buffer solution of pH 2.0.

5. The method of claim 1, characterized in that the eluate resulting from step (c) is dialyzed against a phosphate-buffered saline solution for preparation for step (d).

6. The method of claim 1, characterized in that said immobilized zinc chelate is a chelate of zinc and iminodiacetate coupled to epoxy-activated Sepharose.

7. The method of claim 1, characterized in that the immobilized zinc chelate after adsorption and before elution is washed with a phosphate-buffered saline solution of about neutral pH followed by washing with a buffer solution of lower pH up to pH 5.9.

8. The method of claim 1, characterized in that the elution agent of step (e) has a pH between 6.0 and 4.0 and an ionic strength between 0.05 M and 0.5 M.

9. The method of claim 8, characterized in that elution from the zinc chelate is effected with a 0.1 M sodium acetate solution of pH 4.2.

10. The method of claim 1, wherein said zinc chelate is a zinc chelate gel.

11. The method of claim 1, wherein said porous glass beads have a controlled pore size with an average value of from 170–1700 angstroms.

12. The method of claim 1, wherein said porous glass beads have a diameter of between about 50 μm and about 500 μm.

13. The method of claim 1, wherein said aqueous solution of human fibroblast interferon has a pH between 7.0 and 8.2.

14. The method of claim 1, wherein said immobilized zinc chelate is a chelate of zinc and iminodiacetate coupled to agarose having side chains with terminal epoxy groups.

* * * * *